United States Patent
Pliszka et al.

(10) Patent No.: US 6,811,991 B1
(45) Date of Patent: Nov. 2, 2004

(54) METHOD FOR MEASURING CONCENTRATION OF A CLEANING AGENT IN A WASH LIQUOR

(75) Inventors: Matthew E. Pliszka, Whitefish Bay, WI (US); Leza Luchetta, Madison, WI (US)

(73) Assignee: Environmentally Sensitive Solutions, Inc., Mequon, WI (US)

( * ) Notice: Subject to any disclaimer, the term of this patent is extended or adjusted under 35 U.S.C. 154(b) by 284 days.

(21) Appl. No.: 10/104,225

(22) Filed: Mar. 22, 2002

Related U.S. Application Data

(63) Continuation-in-part of application No. 09/436,619, filed on Nov. 9, 1999, now Pat. No. 6,361,960.

(51) Int. Cl.[7] .................................................. C12Q 1/54
(52) U.S. Cl. ........................................... 435/14; 435/25
(58) Field of Search ................................ 435/14, 4, 25, 435/28; 436/64

(56) References Cited

U.S. PATENT DOCUMENTS

| | | | |
|---|---|---|---|
| 3,958,560 A | | 5/1976 | March |
| 4,867,193 A | * | 9/1989 | Hayashi et al. ............... 137/93 |
| 5,267,152 A | | 11/1993 | Yang et al. |
| 5,459,317 A | | 10/1995 | Small et al. |
| 5,498,546 A | * | 3/1996 | Kuhlmann et al. ........... 436/55 |
| 5,676,143 A | | 10/1997 | Simonsen et al. |
| 6,061,582 A | | 5/2000 | Small et al. |
| 6,361,960 B1 | * | 3/2002 | Pliszka et al. ................ 435/14 |

OTHER PUBLICATIONS

Website printout of www.diabetesnet.com/diabetes_technology/noninvasive_monitoring.html; p 1, 2001.
Website printout of www.futrex.com/dbdesc.html, pp 1–5, 1997.
Website printout of diabetes.about.com/library/weekly/aa121100a.htm, pp 1–2; Dec. 11, 2000.
Website printout of www.sugartrac.com/sugartrac system overview.htm.; pp 1–2, undated.
Website printout of www.animascorp.com/products/pr_glucosesensor.shtml, pp 1–3, 2001.
Website printout of www.diabetes.com/diabetes technology/noninvasive monitoring optiscan.html, pp. 1–2, 2001.
Website printout of www.ohiou.edu/researchnews/SCIENCE/diabetic_light.htm; pp 1–2, Jul. 24, 2000.

* cited by examiner

*Primary Examiner*—Ralph Gitomer
(74) *Attorney, Agent, or Firm*—Godfrey & Kahn, S.C.

(57) ABSTRACT

A method of determining the concentration of a surfactant-based neutral cleaner in a wash liquor, a hand-held apparatus, and a test kit for carrying out the method are provided. According to the method, a cleaner composed of the cleaning agent, an amount of a reducing sugar that is proportional to the cleaning agent, and a sugar preserving agent, is added to a wash solution. The concentration of reducing sugar present in the wash solution may then subsequently be determined by infrared quantitative analysis to provide a concentration of reducing sugar correlative with the amount of cleaning agent remaining in the wash liquor. An apparatus suitable for carrying out infrared quantitative analysis can be packaged with associated test supplies and reagents in a test kit.

7 Claims, 2 Drawing Sheets

METHOD FOR MEASURING CONCENTRATION OF A CLEANING AGENT IN A WASH LIQUOR

CROSS-REFERENCE TO RELATED APPLICATIONS

This is a continuation-in-part application of U.S. patent application Ser. No. 09/436,619, filed Nov. 9, 1999, now U.S. Pat. No. 6,361,960, issued Mar. 26, 2002.

FIELD OF THE INVENTION

The present invention relates to a method, apparatus, and test kit for measuring and monitoring the concentration of a cleaning agent in a liquid, more particularly a surfactant-based neutral cleaning agent in a wash liquor.

BACKGROUND OF THE INVENTION

In commercial cleaning of process oils and grease from metal parts, tools and other metal surfaces commonly found in maintenance departments, auto service shops, and metal processing industries, there has been a shift over the years from solvent washer systems to aqueous-based cleaners. Of those cleaners, alkaline cleaning products have become widely used.

Alkaline cleaners chemically react with most oils by saponification, whereby the oil is chemically changed to a partially soluble soap, which cannot be easily separated from the wash water. A drawback of alkaline cleaning products is that they cannot be discharged to a sewer system due to heavy metals and chelators in the solution. In addition, the high alkaline pH between 8.0 and 12.0 further complicates the wastewater treatment process. Alkalines also become consumed during the saponification process, which necessitates constantly adding more cleaner to replace what has been consumed.

The advent of surfactant-based neutral cleaners (SBNs) has provided a new option for aqueous degreasers for cleaning hard surfaces. SBNs have a neutral use pH of between 7.0 and 8.0, and are all organic, provide superior rinsability, greater foam control, mildness to the skin, longer shelf life, eliminate many wastewater problems and washer corrosion, do not leave the characteristic white film of alkaline products, and provide an "all-in-one" product that is safe on all kinds of metal surfaces. In the area of wastewater treatment, SBNs reduce the need for pH adjustment prior to discharge, thus eliminating the costs associated with acid neutralization. Because of the neutral pH, bioremediation becomes a viable wastewater treatment option. Unlike alkaline degreasers, neutral cleaners clean by a mechanism of emulsification whereby they surround oil molecules with a micelle formed by agitation and impingement of the oily surface. The micelles prevent the oil from re-attaching to the metal surface and, when the agitation stops, release the oil to the surface where it can be removed by traditional recovery methods. Unlike alkalines, once the excess oil is recovered, the neutral soap is available for cleaning again, which extends the life of the bath solution.

In a wash process, it is desirable to monitor the concentration of the cleanser in the wash solution throughout the operation in order to maintain the cleanser at a consistent level. Current methods for testing the concentration of an alkaline detergent in a wash liquor include fluorescence, conductivity and, most commonly for metal cleaners, acid-base titration based on a phenolphthalein indicator end point. A drawback of these methods is that they give an inaccurate analysis due to soil loading. In addition, conductivity must be empirically determined for each detergent.

U.S. Pat. No. 5,498,546 (Kuhlmann et al.) discloses another method for determining the concentration of an alkaline detergent in an industrial laundry wash liquor, by adding a reducing sugar to the wash liquor in an amount proportional to the detergent composition, chemically reacting the sugar with an aromatic hydrazine compound, and photometrically measuring the color. However, the test procedure is time consuming, and requires multiple reagent solutions, heating and temperature control for accurate results, and an extended reaction time to induce a color change. In addition, a PC is needed as an instrument-operator interface, relatively complicated instrumentation is used, the set-up is expensive, and frequent calibration of instruments is required.

Currently used methods for determining the concentration of SBNs in a washer bath are acid-base titration and EDTA titration, which involve adding an indicator to a small volume of the wash solution and measuring the amount of titrant required to induce a color change. Problems with these methods include interference caused by lubricants, oils, rust inhibitors and additives in the washer bath, inconsistent results from bath to bath, the need for multiple chemical reagents, difficulty in distinguishing a color change in a dirty or murky bath, and the need to conduct multiple steps for the analysis. In addition, the use of EDTA in the cleaner formulation as a metal chelator causes wastewater concerns due to increased heavy metal discharge. To date, there are no procedures for readily and accurately testing the concentration of a surfactant-based neutral cleaner (SBN) in a wash liquor.

Therefore, an object of the invention is to provide a method for readily and accurately determining the concentration of surfactant-based neutral cleaners (SBNs) in a wash liquor that overcomes the disadvantages of current testing methods.

SUMMARY OF THE INVENTION

These and other objects are achieved by the present invention, which is directed to a method of determining the concentration of a cleaning agent in a wash liquor, particularly a surfactant-based neutral cleaning agent, an apparatus for carrying out the method, and a test kit containing the apparatus and associated test items and reagents.

According to the method, a wash liquor is combined with a solution containing a mixture of the cleaning agent, an amount of a reducing sugar that is proportional to the cleaning agent, and a sugar preserving agent. The solution of the cleaning agent and reducing sugar preferably contains about 0.5–3.0% reducing sugar, more preferably about 2%. To test for the concentration of the cleaning agent in the wash liquor, an aliquot or portion of the wash liquor is removed and reacted with an enzyme composition to induce an enzymatic reaction with the reducing sugar and produce a colored reaction product. The enzyme composition is typically composed of an oxidase enzyme, peroxidase, and an indicating agent that will produce a colored product when the sugar is reacted with the enzyme composition. In the use of glucose as the reducing sugar, glucose oxidase is a preferred component of the enzyme composition.

The intensity of the color of the enzyme/sugar reaction product can be measured photometrically using light at an appropriate wavelength. The color intensity value is then correlated with the concentration of the reducing sugar, which, in turn, is correlated to the concentration of the cleaning agent in the wash liquor. An approximate concentration of the reducing sugar in the wash liquor can be determined by comparing the color of the reaction product to a color chart.

The method is useful for monitoring the concentration of the cleaning agent in a wash liquor over time by occasionally or at set intervals, removing a portion of the wash liquor, reacting it with the enzyme composition, and measuring and correlating the color intensity of the reaction product to the concentration of the cleaning agent in the wash liquor.

In this embodiment, an aliquot of the wash liquor is deposited onto an enzyme composition that is immobilized on a solid support such as a plastic test strip. The intensity of the color of the reaction product can be determined photometrically by transmitting a beam of light at the desired wavelength onto the solid support and to a light detector that receives the light reflected from the reaction product.

In implementing the method, it is desirable to use a portable, hand-held apparatus that is designed to measure the concentration of the reducing sugar and correlate that amount to the concentration of the cleaning agent in the wash liquor. Such a device includes a member for removably receiving the solid support (test strip), a light source for applying a beam of light at the desired wavelength onto the solid support, and a member for detecting the light reflected from the reaction product on the solid support. The detecting member is operable to produce an output signal that is proportional to the light that is detected. The device further includes a microprocessor that receives and processes the output signal, and is programmed to correlate the output signal to the concentration of the reducing sugar and, preferably, to process and correlate the concentration of the reducing sugar to the concentration of the cleaning agent in the wash liquor. In use of the apparatus, a test strip with the enzyme composition immobilized on it is inserted into the receiving slot, and a drop of the wash liquor is deposited onto the enzyme composition. The enzymatic reaction typically proceeds for about 30–60 seconds, whereupon the apparatus photometrically measures the color intensity of the reaction product and processes the data to arrive at the concentration of the reducing sugar, and preferably the cleaning agent, in the wash liquor. The value is then displayed and/or printed out for the user.

A test kit is provided that contains the portable, hand-held apparatus packaged together with other items and reagents used in the test method. Such items can include test strips with the enzyme system immobilized thereon, instructions for using the apparatus and other testing items according to the method of the invention, a calibration standard curve of the sugar concentration versus the cleaning agent concentration, and, optionally, a container or package of the cleaning agent, reducing sugar and sugar preservative.

In another method according to the present invention, a wash liquor is combined with the solution containing a mixture of the cleaning agent, an amount of a reducing sugar that is proportional to the cleaning agent, and a sugar preserving agent. The solution of the cleaning agent and reducing sugar preferably contains about 0.5 to 3.0% reducing sugar, more preferably about 2%. To test for the concentration of the cleaning agent in the wash liquor, infrared quantitative chemical analysis may be employed to determine the concentration of reducing sugar and, consequently, the concentration of cleaning agent remaining in the wash liquor. A portion of wash liquor including a mixture of the cleaning agent, an amount of reducing sugar proportional to the cleaning agent and a sugar preserving agent may then be irradiated with infrared radiation so that the radiation is transmitted through or reflected from the portion of the wash liquor. Intensity data is then collected from the transmitted or reflected infrared radiation using a detector and the collected data is filtered to isolate a portion of the data indicative of the reducing sugar included in the wash liquor. The portion of the data indicative of the reducing sugar may then be correlated with the concentration of the cleaning agent in the wash liquor.

The present invention may further be in the form of a test kit useful in measuring the concentration of a cleaning agent in a wash liquor utilizing the preceding infrared sampling methodology instructions for operation, maintenance and programming of the apparatus. A sampling apparatus is included with the test kit and includes an infrared radiation source, an infrared radiation detector, and a processing unit capable of filtering data from the detector to isolate a portion of the data indicative of the reducing sugar included in the wash liquor. The sampling apparatus may then be further capable of displaying to a user the concentration of the reducing sugar present in the wash liquor. The apparatus may be further capable of correlating the concentration of the reducing sugar with the concentration of cleaning agent present in the wash liquor and displaying to a user the concentration of the cleaning agent. The test kit may also include instructions for measuring the concentration of reducing sugar in the wash liquor and instructions for correlating the concentration of the reducing sugar with the concentration of cleaning agent present in the wash liquor. The test kit may further include instructions for operation, maintenance and programming of the apparatus. A container of a mixture of the cleaning agent, an amount of reducing sugar in known proportion of the cleaning agent, and a sugar preserving agent may also be provided with the kit for the convenience of the user.

Advantageously, the present method provides a quick, easy, accurate, and reliable assay for testing the concentration of a surfactant-based neutral cleaner in a wash liquor. The assay employs an indicating agent, i.e., the reducing sugar, which is biodegradable and non-toxic, eliminates the need for hazardous chemical reagents, and will not affect the wash process or cleanliness of the part or item being cleaned. The present method also decreases the time required for testing the amount of cleaner in a wash liquor, and requires the use of relatively inexpensive instrumentation.

BRIEF DESCRIPTION OF THE DRAWINGS

Throughout the following views, reference numerals will be used on the drawings, and the same reference numerals will be used throughout the several views and in the description to indicate same or like parts of the invention.

DETAILED DESCRIPTION

Figure 1:
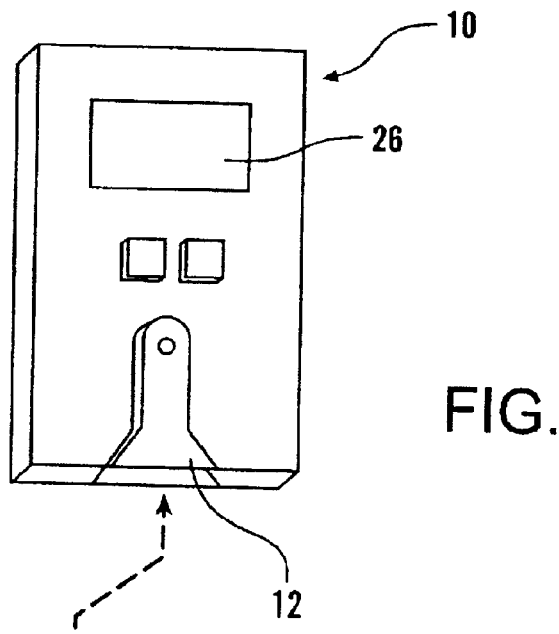
FIG. 1 is a perspective view of an apparatus for use in determining the concentration of a cleaning agent in a wash liquor according to the present invention.

The invention provides a rapid and simple assay for reliably determining the concentration of a surfactant-based neutral cleaner in a wash liquor, and an apparatus and test kit for use in the method. The method can also be used to measure the concentration of other process chemicals such as those classified as aqueous-based lubricants, coolants, rust inhibitors, derusting agents, defoamers, among others.

The term "wash liquor" as used herein is a water-based solution that includes a cleaning agent, typically at a use concentration of about 1–10%. A typical wash liquor made with a surfactant-based neutral cleaner is a water-based solution composed of surfactants, propylene glycol ethers, rust inhibitor and preservatives.

According to the invention, a reducing sugar is combined with the cleaning agent, and the mixture is then added to the wash liquor. The wash liquor containing the cleaning agent has a pH of about 6.0–8.5. Glucose is the preferred reducing sugar, although other reducing sugars such as fructose, maltose, galactose, and lactose can also be used. Preferably the reducing sugar/cleaning agent mixture is formulated to include about 0.5–3.0% by weight sugar (or about 5–30 gm/l), preferably about 1–2% by weight, most preferably about 2% by weight. By combining the reducing sugar with the cleaning agent and adding the mixture to the wash liquor, rather than directly adding the sugar alone to the wash liquor, it is assured that the amount of reducing sugar that is present in the wash liquor is proportional to the concentration of the cleaning agent. This provides for a reliable indirect measurement of the cleaning agent in the wash liquor.

The reducing sugar and cleaning agent solution further includes a preservative such as sodium benzoate, to inhibit microbial degradation of the sugar. The inclusion of a sugar-preserving agent helps maintain a constant amount of sugar in the concentrated cleaning agent/reducing sugar solution and in the wash liquor by preventing degradation of the sugar. Preferably, the cleaning agent/reducing sugar solution includes about 0.4–6% sodium benzoate or other preserving agent, preferably about 1–3%, preferably about 2%.

In one embodiment of the present invention, a sample or aliquot of the wash liquor is removed and reacted with an enzyme composition at a temperature and for a time effective to induce an enzymatic reaction with the reducing sugar resulting in a colored reaction product. The assay does not require close temperature control for accurate results and can be run over a wide temperature range (about 70–160° F.). The color intensity of the reaction product is then measured and correlated to the concentration of the reducing sugar and to the cleaning agent in the wash liquor.

In this embodiment of the invention, an aliquot of the wash liquor containing the reducing sugar is placed onto a solid support on which an enzyme composition is immobilized. The enzyme composition typically includes an oxidase enzyme, peroxidase, and an indicator compound that undergoes a reaction with the peroxidase to produce a colored, light-absorbing product. Where the reducing sugar is glucose, the enzyme composition can be composed of glucose oxidase, peroxidase, and an indicator compound such as O-dianisidine, O-tolidine, benzidine, an MBTH-DMAB (3-methyl-2-benzothiazolinone hydrazone hydrochloride and 3-dimethylaminobenzoic acid) dye couple, an AAP-CTA (4-aminoantipyrene and chromotropic acid) dye couple, O-toluidine, 2,2'-azinodi-(3-ethylbenzthiazoline sulphonic acid-6), 3-methyl-2-benzothiazolinone hydrazone plus N,N-dimethylaniline, phenyl plus aminophenazone, sulfonated 2,4-dichlorophenol plus 4-aminophenazone, 2-methoxy-4-allyl phenol, and 4-aminoantipyrene-dimethylaniline, among others. Such glucose test strips are commercially available, for example, under the tradename One Touch® test strips, from Lifescan, Inc., Mountain View, Calif., and are composed of about 14 IU/cm$^2$ glucose oxidase, about 11 IU/cm$^2$ peroxidase, about 0.06 mg 3-methyl-2-benzothiazolinone hydrazone hydrochloride (MBTH), and about 0.12 mg 3-dimethylaminobenzoic acid (DMAB).

When the sample of the wash liquor containing the reducing sugar is brought into contact with the enzyme composition, preferably at about room temperature, the enzyme reagent chemically reacts with the reducing sugar to produce a colored reaction product and a change in reflectance that indicates the concentration of the reducing sugar in the sample. For example, with glucose as the reducing sugar, the glucose oxidase enzyme oxidizes the glucose to gluconic acid forming hydrogen peroxide as a reaction product, and the peroxidase enzyme catalyzes an oxidative coupling of the hydrogen peroxide with the indicator compound which undergoes a color reaction to give a color proportional in intensity to the glucose level in the sample. The liquid sample remains in contact with the enzyme composition for an effective reaction time for color development, typically about 30–60 seconds.

Although not preferred due to low precision and accuracy compared to the photometric method, an approximate concentration of the reducing sugar can also be determined by visually comparing the color of the enzyme/sugar reaction product to a standard color chart calibrated to various concentrations of the reducing sugar, and matching the color of the sample with the corresponding color zone on the chart, which represents a range of values. Paper and/or plastic test strips containing the enzyme composition are useful in a visual comparison of the color of the reaction product. Such test strips are commercially available and include, for example, Diastix® reagent strips from Bayer Corporation, Elkhart, Ind. (2.2% w/w glucose oxidase, 1.0% w/w horseradish peroxidase, 8.1% w/w potassium iodide, 69.8% w/w buffer, 18.9% w/w non-reactive ingredients).

The color intensity of the reaction product is determined by means of an instrument such as a diffuse reflectance spectrophotometer with associated software that reads reflectance, and calculates and correlates the color intensity to the level of the reducing sugar in the liquid sample. The device can provide a readout of the sugar concentration, which can then be correlated to the concentration of the cleaning agent in the wash liquor according to a standard curve or calibration graph of sugar concentration vs % cleaner in the wash liquor. In one embodiment, the device is further programmed to correlate the concentration of the reducing sugar to the concentration of the cleaning agent in the wash liquor based on the proportional amount of the reducing sugar in the sugar/cleaning agent mixture that was added to the wash, or using a calibration curve programmed into the device.

In one method, a portable, hand-held apparatus is used to photometrically measure the intensity of the enzyme color reaction product on a solid support such as a transparent test strip. An example of such a device is described, for example, in U.S. Pat. No. 5,304,468, and commercially available as the One Touch® blood glucose monitoring System from Lifescan, Inc., Mountain View, Calif. Such a commercial device will provide a read-out of the concentration of the reducing sugar in the test sample, which can then be correlated to the concentration of the cleaning agent in the wash liquor, based on an established standard curve.

Figure 2:
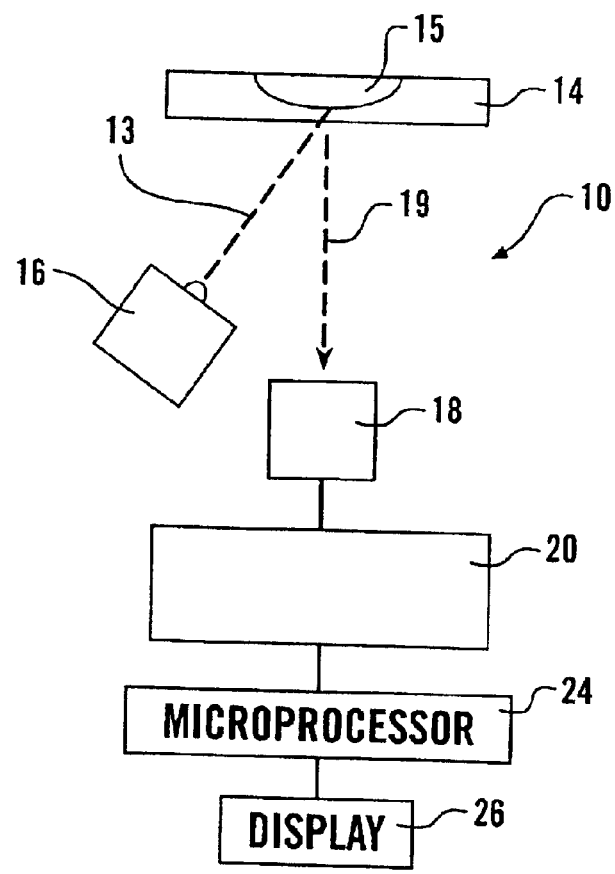
FIG. 2 is a schematic of the apparatus of FIG. 1.

As depicted in FIGS. 1 and 2, such an apparatus 10 includes a member 12 for removably receiving a test strip (solid support) therein, a light source 16 such as a high intensity LED for applying a beam of light 13 to the test strip 14 at a suitable wavelength according to the absorption of the colored reaction product, a member 18 for detecting the light 19 reflected from the test strip 14 such as a phototransistor that produces an output signal (current) proportional to the light it receives. Test strip 14 has an enzyme system 15 immobilized thereon, and receives an aliquot of wash liquor for reaction with the enzymes to produce the enzymatic reaction product. An electronics component 20 such as a linear integrated circuit, converts the current to a voltage and to a digital signal to be received by a microprocessor 24. The microprocessor 24 is composed of components to store and process the data from the reflectance measurements to arrive at the concentration of the reducing sugar, and output that data to a digital display 26. The display 26 is preferably a LCD or LED display.

According to the invention, for a direct readout of the concentration of the cleaning agent in the wash liquor, the microprocessor 24 can be further programmed to correlate the concentration of the reducing sugar to the concentration of the cleaning agent in the wash liquor according to a set of predetermined values based on the proportional amounts of the reducing sugar and cleaning agent in the sugar/cleaning agent mixture that was added to the wash liquor.

In the use of such a portable device 10 to monitor the amount of a cleaning agent in a wash liquor accordingly to the present method, a test strip 14, preferably a mylar or other plastic strip that is light transmissive, having the enzyme composition 15 immobilized thereon is inserted into the slot in the receiving member 12 for the test strip 14 (solid support) and aligned with the light source 16. An aliquot of the wash liquor, preferably a drop or about 0.05 ml, is placed on the test strip 14 and allowed to react with the enzyme reagent 15 to form an immobilized colored reaction product. The apparatus 10 is then activated to photometrically measure the color intensity of the reaction product at an appropriately set wavelength. The data processor 24 then correlates intensity of the color of the reaction product to the concentration of the reducing sugar in the wash liquor, which, being proportional to the amount of the cleaning agent, is then correlated to the concentration of the cleaning agent in the wash liquor.

The portable, hand-held apparatus 10 can be packaged in a test kit or article of manufacture, together with one or more of the following items: a container of the cleaning agent combined with a proportional amount of the reducing sugar, a package of test strips with the enzyme composition immobilized thereon, instructions for using the foregoing items for measuring the concentration of the cleaning agent added to a wash bath or other liquid, a calibration standard curve of the concentration of the reducing sugar to the % cleaner in the wash liquor, Material Safety Data Sheet (MSDS), and pipettes and other like tools for use in the assay. In a preferred form, the cleaning agent/sugar mixture is composed of a surfactant-based neutral cleaner combined with about 2% glucose, and the enzyme composition is composed of glucose oxidase, peroxidase, and an indicator component.

Alternative technologies, other than enzymatic approaches, may be used to quantify the amount of reducing sugar present in a wash liquor according to the present invention. In a preferred embodiment of the invention, infrared quantitative chemical analysis is used to determine the concentration of reducing sugar and, subsequently, the concentration of cleaning agent remaining in the wash liquor. Infrared analysis, an emerging non-invasive sampling technique, is based on the detection of distinct and reproducible vibrational frequencies in chemical bonds between a molecule's atomic constituents. Organic compounds such as fat, protein, or glucose, having a plurality of chemical bonds, are known to each possess unique patterns, or optical signatures, when measured at defined infrared wavelengths. By probing a substance with infrared light and by accurately measuring the resultant reflected or transmitted spectrum, one can not only qualitatively identify but can also quantitatively determine the concentration of chemical constituents within a sampled substance. Many examples of devices and methods capable of performing non-invasive infrared chemical analysis exist in the prior art and are considered to be amenable to being used in quantifying reducing sugar in the present invention.

Suitable examples of infrared devices useful in the present invention include U.S. Pat. Nos. 5,459,317 and 6,061,582, which disclose a non-invasive measurement method and apparatus for the detection and quantification of physiological chemicals, particularly glucose. A signal processing system is described that permits the construction of a device suited for home use. The level of a selected physiological chemical in a test subject is determined in a non-invasive and quantitative manner by a method comprising the steps of: (a) radiating a portion of the test subject with near-infrared radiation such that the radiation is transmitted through or reflected from the test subject; (b) collecting data concerning the transmitted or reflected infrared radiation using a detector; (c) digitally filtering the collected data to isolate a portion of the data indicative of the physiological chemical; and (d) determining the amount of physiological chemical in the test subject by applying a mathematical model to the digitally filtered data.

Further useful examples include U.S. Pat. No. 3,958,560, which describes a glucose sensor to determine the glucose level in patients for use in treating or diagnosing diabetes. In addition, U.S. Pat. No. 5,267,152 describes a method and apparatus for measuring blood glucose concentration by eradicating blood vessels with electromagnetic radiation. The method and apparatus utilize near-infrared radiation, diffuse-reflection laser spectroscopy. Finally, U.S. Pat. No. 5,676,143 is directed to an apparatus for determination of a glucose concentration in a biological matrix. U.S. Pat. Nos. 5,459,317, 6,061,582, 3,958,560, 5,267,152, and 5,676,143 are incorporated herein by reference.

Figure 3:
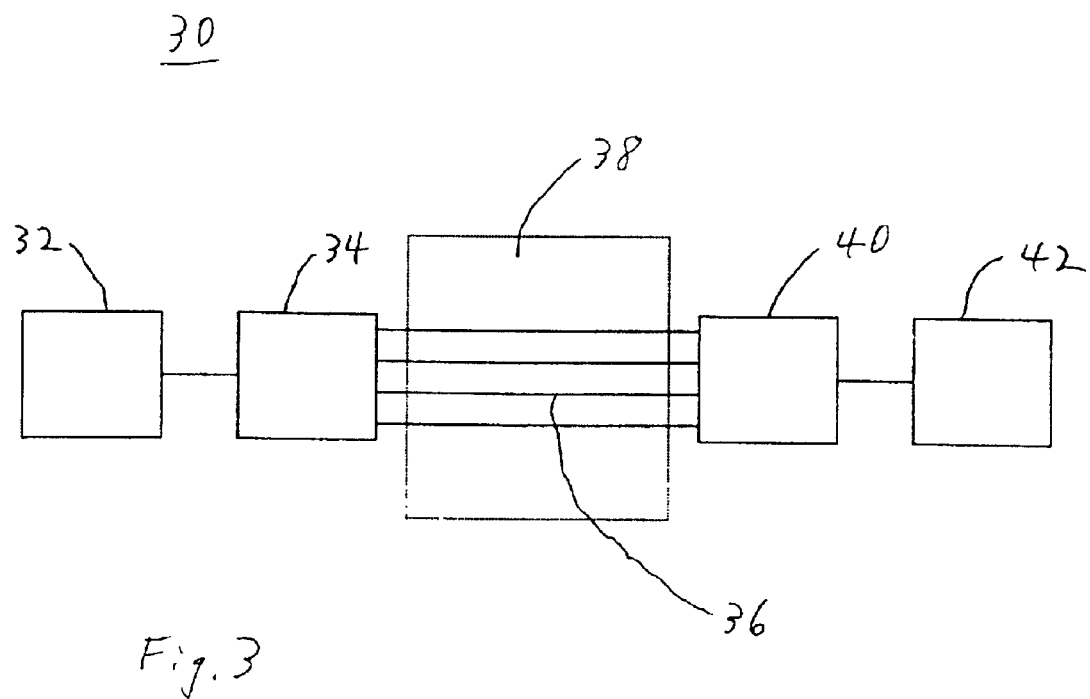
FIG. 3 is a schematic representation of an infrared device suitable for infrared measurement of a reducing sugar in a wash liquor according to the present invention.

FIG. 3 is a schematic representation of an infrared device 30 suitable for use in the present invention for non-invasive, infrared measurement of a reducing sugar, preferably glucose, in a wash liquor. System 30 includes a power source 32 electrically connected and supplying power to a radiation source 34. Radiation source 34 is capable of providing suitable infrared radiation that coincides with the vibrational frequencies of glucose or other reducing sugar being measured. For glucose, the suitable radiation may be adjusted to coincide with the vibrational frequencies characteristic of glucose in the spectral regions of 4,000–5,000 $cm^{-1}$ and 5,800–6,500 $cm^{-1}$. Suitable radiation sources are well known in the field and may be, for example, a tungsten-halogen lamp.

Radiation source 34 provides infrared radiation 36 in a directed manner through or toward sample portion 38 of the wash liquor so that either a transmittance or reflectance spectrum may be generated and collected by a radiation detector 40. As infrared measurements may be conducted based on either a transmittance spectrum or a reflectance spectrum, as illustrated in the example prior art cited above, there is provided a considerable latitude in the manner in which the infrared radiation may impinge on the sample.

Therefore, the physical configuration of the detector schematically shown in FIG. 3 may vary considerably. Specifically, a dual beam system with source 34 and detector 40 arranged co-linearly, instead of in an opposing fashion, is within the infrared detection systems useful in the present invention. The specific nature of the detector 40 is not critical, provided it is capable of detecting the pertinent wavelengths of radiation and responding rapidly enough to be compatible with the other components of the sensor system 30. A detector suitable for use in the present invention is disclosed in U.S. Pat. No. 6,061,582, discussed above and incorporated herein by reference.

In FIG. 3, detector 40 collects radiation 36, generates a corresponding signal, and communicates the signal with a read-out device 42. Read-out device 42 is programmed to receive the signal and subsequently display the amount of reducing sugar present in the sample 38. References discussed above and incorporated herein by reference provide representative guidance regarding the programming of a read-out device 42. System 30 will preferably be contained within a hand-held unit for the user's convenience. Subsequent to the display of the amount of reducing sugar present in sample 38, the user may then correlate the amount of reducing sugar with the amount of cleaning agent present in the wash liquor, perhaps with the aid of instructions provided with the infrared sampling apparatus.

Alternatively, it is envisioned that the infrared sampling apparatus useful in carrying out the invention may further include a read-out device 42 including a processing unit capable, by itself or with the addition of further well known computing means, of correlating the concentration of the reducing sugar with the concentration of cleaning agent present in the wash liquor. The actual concentration of the cleaning agent, in contrast to the amount of reducing sugar, may then be provided to the user thereby requiring no further calculations of the user to equate the amount of remaining reducing sugar to the amount of remaining cleaning agent. Computing means and model calculations for correlating the concentration of the reducing sugar with the concentration of clean agent present in the wash liquor are widely known in the field.

In operation, it is envisioned that sample 38 may have a glucose concentration determined simply by bringing sample 38 within a beam of infrared radiation 36 emitted by system 30. Specifically, sample 38 may be placed in a test chamber, possibly a cuvette, and the cuvette positioned between the source 34 and the detector 40. Alternatively, radiation source 34 and radiation detector 40, or portion thereof, may be immersed in a large volume of sample 38, the sample 38 being continuous with a large volume of wash liquor. A yet further alternative requires no test chamber and no physical contact of the detecting apparatus with the sample. This embodiment simply calls for the infrared emission to be directed at the sample 38, where the relative positioning of detector 40 and source 34 are based on the respective angles of infrared radiation reflectance or transmittance in relation to sample 38. A continuous flow sampling arrangement is also within the scope of the present invention. As described previously, source 34 and detector 40 may be arranged in co-linear fashion where reflectance is being measured.

The infrared apparatus described herein for carrying out the invention may be packaged in a kit form. The kit, similar to the kit embodiment described above for the enzymatic-based method, may contain a mixture including the cleaning agent, an amount of reducing sugar in known proportion to the cleaning agent, and a sugar preserving agent. Including such components with the kit would provide a convenience to the user in carrying out the above-described method.

The invention has been described by reference to detailed examples and methodologies. These examples are not meant to limit the scope of the invention. Variations within the concepts of the invention are apparent to those skilled in the art. The disclosures of the cited references throughout the application are incorporated by reference herein.

What is claimed is:

1. A method of measuring concentration of a cleaning agent in a wash liquor, comprising:
    a) providing a wash liquor comprising a mixture of the cleaning agent, an amount of a reducing sugar proportional to the cleaning agent, and a sugar preserving agent;
    b) irradiating a portion of the wash liquor with infrared radiation such that the radiation is transmitted through or reflected from the portion of the wash liquor;
    c) collecting intensity data related to the transmitted or reflected infrared radiation using a detector,
    d) filtering the collected data to isolate a portion of the data indicative of the reducing sugar included in the wash liquor, wherein a concentration of the reducing sugar is determined directly from the portion of the data indicative of the reducing sugar included in the wash liquor; and
    e) correlating the portion of the data indicative of the reducing sugar with the concentration of the cleaning agent in the wash liquor.

2. A method according to claim 1 wherein the cleaning agent is a surfactant-based neutral cleaner.

3. A method according to claim 1 wherein the cleaning agent is selected from the group consisting of a water-based lubricant, coolant, rust inhibitor, defoamer, and derusting agent.

4. A method according to claim 1 wherein the mixture of step a) comprises about 0.5 to about 3.0% reducing sugar.

5. A method according to claim 1 wherein the mixture of step a) comprises about 2% reducing sugar.

6. A method according to claim 1 comprising the further step of monitoring the concentration of cleaning agent over time by repeating steps a) through e) at time intervals.

7. A method according to claim 1 wherein the wash liquor containing the cleaning agent has a pH of about 6.0 to about 8.5.

* * * * *